United States Patent [19]

Worrell

[11] 4,296,263

[45] Oct. 20, 1981

[54] TERTIARY BUTYL ALCOHOL PRODUCTION

[75] Inventor: G. Richard Worrell, Media, Pa.

[73] Assignee: Atlantic Richfield Company, Los Angeles, Calif.

[21] Appl. No.: 188,653

[22] Filed: Sep. 19, 1980

[51] Int. Cl.³ .......................................... C07C 27/12
[52] U.S. Cl. .................................................. 568/910
[58] Field of Search ........................................ 568/910

[56] References Cited

U.S. PATENT DOCUMENTS

| | | | |
|---|---|---|---|
| 2,780,654 | 2/1957 | Robertson et al. | 568/910 |
| 2,845,461 | 7/1958 | Winkler et al. | 568/910 |
| 2,862,973 | 12/1958 | Winkler et al. | 568/910 |
| 3,478,108 | 11/1969 | Grane | 568/910 |
| 3,816,548 | 6/1974 | Williams et al. | 568/910 |
| 3,825,605 | 7/1974 | Johnston | 568/910 |
| 3,829,510 | 8/1974 | Adams et al. | 568/910 |
| 3,832,149 | 8/1974 | Kozlowski et al. | 568/910 |
| 4,239,926 | 12/1980 | Grane et al. | 568/910 |

OTHER PUBLICATIONS

Winkler et al., "Ind. & Eng. Chem.", vol. 53, No. 8, Aug. 1961, pp. 655-658.

Primary Examiner—Joseph E. Evans
Attorney, Agent, or Firm—John R. Ewbank

[57] ABSTRACT

A liquid mixture of normal butane and isobutane is catalytically oxidized at 15–45% conversion of the isobutane per pass at conditions favoring selective oxidation of the isobutane with minimized oxidation of the normal butane, thereby eliminating the need for superfractionation for ultrapurification of the isobutane prior to the oxidation step. Conditions include 260°–340° F., 200–1000 psig, 1–10 hour residence time, 1–500 ppm of catalyst selected from distributable (e.g. soluble) forms of chromium, cobalt, nickel, manganese, molybdenum, and mixtures thereof.

1 Claim, 1 Drawing Figure

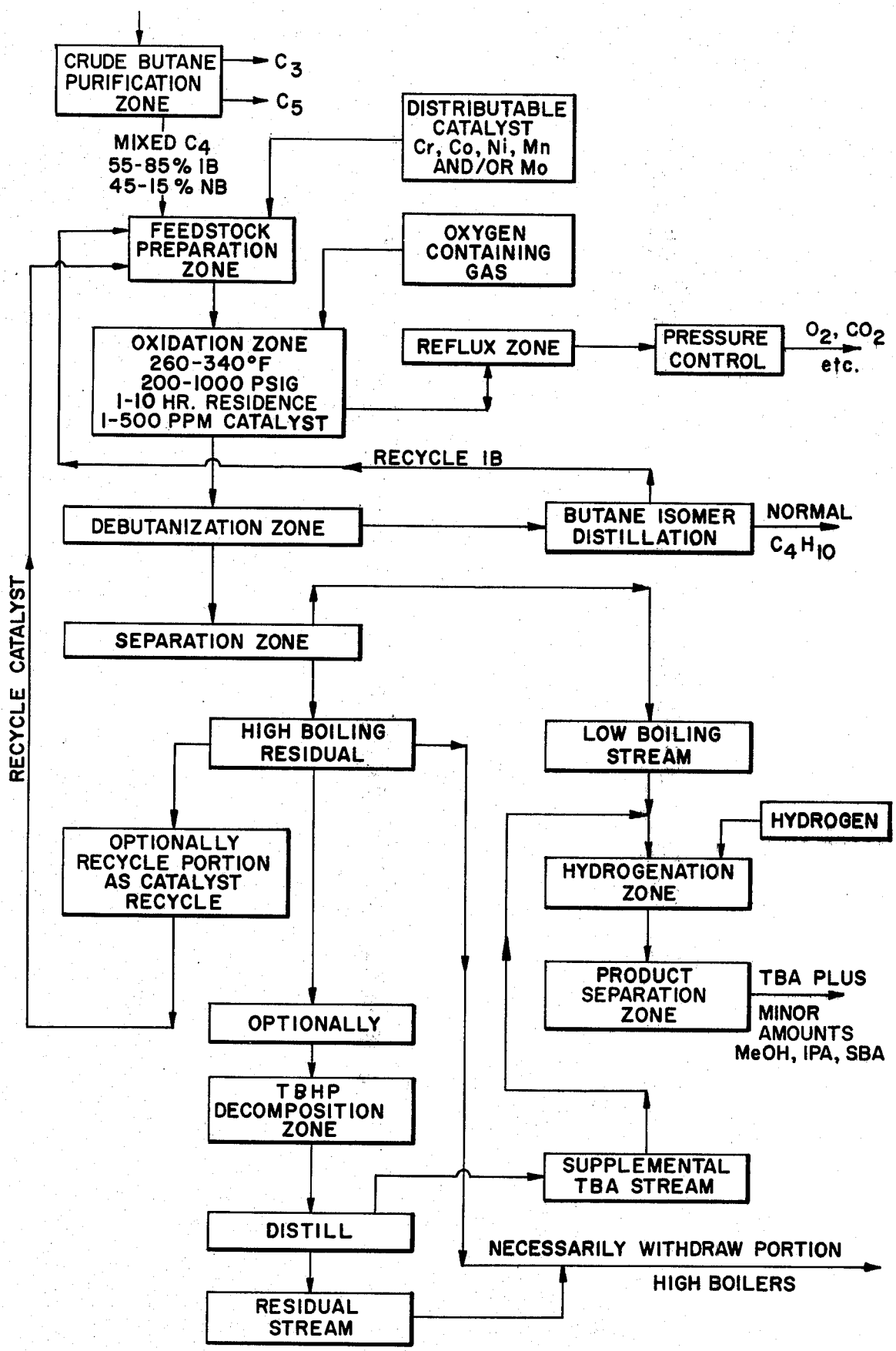

TERTIARY BUTYL ALCOHOL PRODUCTION

RELATED APPLICATIONS

Reference is made to several copending applications of Henry R. Grane, John C. Jubin, and G. Richard Worrell, including Ser. No. 051,561 filed June 25, 1979, now U.S. Pat. No. 4,239,926, abandoned Ser. No. 45,454 filed June 4, 1979, which was replaced by continuation Ser. No. 124,035 filed Feb. 25, 1980, and abandoned Ser. No. 45,365 filed Feb. 20, 1980, which was replaced by continuation Ser. No. 124,404 filed Feb. 25, 1980, each of which cases is being incorporated herein and deemed here reiterated.

FIELD OF INVENTION

This invention relates to the selective oxidation of isobutane with an oxygen containing gas to produce tertiary butyl alcohol.

PRIOR ART

Robertson et al U.S. Pat. No. 2,780,654 is among the many patents recommending catalytic vapor phase oxidation of IB (i.e. isobutane) to TBA (i.e. Tertiary Butyl Alcohol).

Winkler et al U.S. Pat. No. 2,845,461 explains that liquid phase non-catalytic oxidation of isobutane yields a mixture of TBA and tertiary butyl hydroperoxide (i.e. TBHP) with great emphasis upon the high value of TBHP.

Winkler et al U.S. Pat. No. 2,862,973 notes that isoparaffins are selectively oxidized to dialkyl peroxides even when minor amounts of corresponding normal hydrocarbons are present, but teaches that only trace amounts of such normal hydrocarbons should be employed in the feedstock.

Williams et al U.S. Pat. No. 3,816,548 describes the oxidation of liquid IB at 600 psig at 257° to 392° F. for 2 to 6 hours using 2 to 500 ppm catalyst of the phthalocyanine type (Cu, Co, Fe, Mn, and/or mixtures) to prepare TBA.

Johnston U.S. Pat. No. 3,825,605 employs an alumina supported hydrogen-treated cobalt molybdate type of catalyst to oxidize liquid IB to TBA.

Kozlowski et al U.S. Pat. No. 3,901,664 describes a motor fuel comprising a mixture of low-boiling non-aromatic hydrocrackate and a crude TBA comprising some methanol and some isopropanol.

Adams et al U.S. Pat. No. 3,829,510 describes the preparation of an oxylate of the type used in said Kozlowski et al fuel. IB is oxidized to prepare a crude TBA which is hydrogenated to convert acetone to isopropanol. The Adams et al method emphasizes recycling of the methyl esters. The oxidation features 220° to 280° F. at 600 psig at 30 to 40% conversion using cobalt acetate, lead acetate, cadmium acetate, magnesium acetate and/or mixtures thereof to catalyze the oxidation, and using at least 92% nitrogen in the oxygen containing gas to repress propensities toward explosions.

The difference in boiling points at atmospheric pressure between IB and normal butane is only about 18° F., but the separation of streams containing only about 55 to 85% pure isomer requires relatively low capital investment, relatively low utility costs, and overall moderate expense. However, in order to distill mixed butanes to obtain isomer streams having more than 99% purity, the 18° F. difference in boiling points is so small that the equipment cost, energy consumption, and overall costs are so great that the cost of a stream of ultrapurified IB can be deemed to be considerably greater than the cost of a technical grade of IB containing e.g. 16% normal butane.

In producing TBHP from IB, ultrapurification of IB is worthwhile because each 1% of normal butane in the feedstream measurably decreases the rate of formation of TBHP. Substantially all other reactions involving IB are also adversely affected by the presence of minor amounts of normal butane. Because of this long established importance of the purity of IB, substantially all research featuring IB has utilized ultrapurified IB containing less than 3% normal butane. Purified grades of IB having from 3 to 15% normal butane are more costly than mixed butanes containing 15 to 49% normal butane and 51 to 85% isobutane.

Prior to about 1920, substantially all of the IB derived from natural gas and crude petroleum, in which the ratio of IB to normal butane tends to be relatively small. In the 1970's, however, much of the mixed butanes in some refineries was derived from the hydrocracker. Sometimes the mixed butane by-product from a hydrocracker contains about 55% isobutane, and hence can cheaply be upgraded to a stream containing about 80% IB.

Researchers concerned with preparing TBA from IB have continued to employ the ultrapurified grades of IB. Technical literature indicates that there has never been commercialization of any process for making secondary butyl alcohol (SBA) and/or normal butyl alcohol (NBA) by oxidation of normal butane. Instead, the preparation of SBA by hydration of normal butene has been widely practiced, notwithstanding the significant higher cost attributable to using normal butene instead of normal butane as feedstock. Much of the TBA used in gasoline has been a by-product from methods featuring TBHP. However, the demand for TBA for gasoline usage has stimulated the engineering design for a significant variety of plants producing TBA alone. There has been a long-standing demand for an economical method of preparing a gasoline grade TBA from IB, but a long standing failure of the industry to satisfy this demand.

SUMMARY OF INVENTION

In accordance with the present invention, TBA is prepared from an IB stream containing from about 15% to 45% normal butane. Such use of a mixed butane stream eliminates the need for ultrapurification of the IB for the feedstream. Some methyl ethyl ketone is formed as a by-product of using normal butane in the feed. However, hydrogenation of such methyl ethyl ketone (MEK) leads to formation of secondary butyl alcohol (SBA), which is a useful component in gasoline.

The mixed butanes are oxidized in the liquid state at a predetermined pressure within the range from about 200 to about 1000 psig at a predetermined temperature within a range from 260° F. to 340° F. in the presence of 1 to 500 ppm of a catalyst selected from the group consisting of chromium, cobalt, nickel, manganese, molybdenum, and mixtures thereof for a conversion of from about 15% to 45% per pass and for a residence time of from about 1 to about 10 hours. A portion of the reaction mixture is withdrawn as liquid effluent from the oxidation zone, and is debutanized in a debutanization zone where the major amount of butanes are distilled from a residual oxygenated organic liquid. The volatilized butanes are distilled in an isomer distillation zone to separate an overhead stream of recycle IB from a residual stream of normal butane, withdrawn as a by-product. Such separation of the isomers in a butane isomer distillation zone is inexpensive because up to about 45% of the other isomer can be tolerated in each stream from such separation, thus making it a less costly separation than ultrapurification of each isomer.

The residual oxygenated effluent from the debutanization zone liquid is directed to the combination of steps of separation and then hydrogenation.

The liquid effluent from the debutanization is subjected to a separation zone wherein TBA and lower boiling components are separated from a residual stream of by-products boiling higher than about 194° F. The residual liquid can include water, formic acid, secondary butyl alcohol (SBA), acetic acid, and other highboiling by-products. Some by-products are withdrawn as by-products and used in whatever manner seems appropriate. Esters of $C_1$-$C_4$ alcohols with formic acid, acetic acid, etc., are among such miscellaneous by-products.

The overhead from the separation zone is directed to the hydrogenation zone. Such overhead is hydrogenated in a hydrogenation zone at mild conditions favoring minimized hydrogenation of TBA to IB and significant conversion of acetone to isopropyl alcohol. A catalyst of 5% copper on sorptive alumina can be used at about 200° F. at about 50 psig hydrogen at a velocity of about 20 weights of liquid per weight of catalyst per hour. The effluent from the hydrogenation zone provides a product stream having TBA as the principal component and measurable amounts of methanol, isopropanol, and possibly other components.

The features of the invention are further clarified by reference to a plurality of examples.

DESCRIPTION OF EMBODIMENTS

Example I

An oxidation reactor is maintained at 650 psig at 300° F. The liquid in the reactor comprises isobutane, acetone, methanol, tertiary butyl alcohol, normal butane, tertiary butyl hydroperoxide, secondary butyl alcohol, methyl ethyl ketone, water, formic acid, acetic acid, methyl formate, methyl acetate and related by-products as well as dissolved gases such as oxygen, carbon monoxide, and carbon dioxide. A mixture of fresh mixed butanes (i.e. normal butane plus isobutane) and recycle isobutane is modified by the addition of catalyst in a feedstream preparation zone and then injected into the reactor liquid. An oxygen containing gas is injected into the liquid reaction mixture, which contains 5 ppm of soluble chromium catalyst. Alternatively, the catalyst may be selected from the group consisting of chromium, cobalt nickel, manganese, molybdenum and/or mixtures thereof. The predetermined residence time for the isobutane in the reactor is about 1.5 hours, and the extent of conversion of the isobutane is about 27%. The by-products and products from such oxidation of the mixed butanes include tertiary butyl alcohol (TBA), tertiary butyl hydroperoxide (TBHP), acetone, methanol (all attributable to the selective oxidation of IB) plus minor amounts of secondary butyl alcohols (SBA), methyl ethyl ketone (MEK), normal butyl alcohol (NBA) water, acetic acid, formic acid, esters of the acids and alcohols, and related components. The SBA, MEK, and NBA result from the slight oxidation rate for normal butane. In addition to such liquid products, carbon monoxide and carbon dioxide may be among the by-products which are gaseous at the conditions of pressure and temperature which liquefy normal butane. The degasified liquid reaction mixture can be deemed to be about 73% mixed butanes and about 27% of said liquid mixture of products and by-products.

The reactor is maintained and operated in the manner corresponding generally to the operation of the reactors for production of a mixture of TBHP and TBA except that; (a) mixed butanes instead of ultrapurified IB are employed as feed; (b) a chromium catalyst is present; (c) the temperature is higher; and (d) the rate of product withdrawal is greater so that the residence time is less than when the process is aimed particularly at TBHP. The liquid reaction mixture is adequately agitated so that the average composition of the reaction mixture and the composition of the slip stream from the reactor may be treated as identical.

The liquid stream withdrawn from the oxidation zone is directed through a plurality of processing steps. Normally gaseous components, comprising oxygen, and carbon dioxide are separated and discharged through the pressure regulator in the refluxing zone. Said liquid effluent from the oxidation zone is directed to a debutanization zone, from which the oxygenated organic liquid is directed to a separation zone.

The liquid effluent from the debutanization zone is directed to a separation zone, ordinarily a product distillation zone. An overhead vapor stream includes a variety of components boiling below 194° F., including TBA, b.p. 181° F., methanol 149° F., etc. The concentration of the tertiary butyl hydroperoxide (TBHP) in the residual liquid from said product separation may be high enough to justify an optional zone for decomposition of TBHP. The effluent from the TBHP decomposition zone (if there is such an optional zone) is distilled to provide a supplemental TBA stream and a residual liquid stream. Either or both of the residual liquid streams (from distillation of the debutanized oxidate and from distillation of the effluent from the TBHP decomposition zone) can be allocated between the portion of high boiling stream directed to the feedstream preparation zone as catalyst recycle and the portion of the high boiling stream withdrawn from the process as a purge stream. The supplemental TBA stream is directed to the liquid stream entering the hydrogenation zone.

The overhead from the separation zone flows to a hydrogenation zone in which the conditions are so mild that ketones (acetone and methyl ethyl ketone) are selectively hydrogenated to secondary alcohols with minimized conversion of TBA to IB. The mild hydrogenation is conducted at 250° F. to a total pressure approximately equal to the total pressure in the oxidation zone, the partial pressure of hydrogen usually being several hundred psig. The space rate is about 20 weights of liquid per weight of catalyst per hour, using a 5% copper on sorptive alumina catalyst. The propensity of the TBA to be hydrogenated to IB is repressed, so that the measured amount of TBA in the stream is substantially the same before and after the hydrogenation step. Substantially all of the ketone (i.e. acetone and methyl ethyl ketone) content is thus hydrogenated to the corresponding secondary alcohol, so that the ketone content of the effluent from the hydrogenation zone is not significant enough to require listing, in the recitation of important ingredients.

The mixed butane stream separated in the debutanization zone is directed to a butane isomer distillation zone.

The overhead from such distillation is an isobutane stream directed toward the pumps which recycle the isobutane to the feedstream preparation zone. The bottoms from such isomer distillation is withdrawn from the process as a normal butane stream. Particular attention is directed to the fact that no ultrapurification is necessary in the butane isomer distillation zone. Hence, the cost is significantly less because the recycled isobutane stream can tolerate significant amounts (e.g. 16%) of normal butane without jeopardizing the overall process.

The presence of measurable amounts of tertiary butyl hydroperoxide in the oxidation zone is believed to be helpful in promoting conversion of isobutane to isobutyl alcohol. An increased TBHP concentration in the oxidation zone is attainable because of said recycling of a high boiling stream containing TBHP. Because high boiling by-products such as acetic acid, formic acid, etc. must not be allowed to accumulate in excessive concentrations in the liquid in the oxidation zone, it is necessary to withdraw a purge stream of liquid from the process. The concentration of high boiling products in the effluent from the debutanizing zone must be within a range from about 1% to about 10% of the liquid oxidate. The proportion of purge stream withdrawal is increased significantly whenever there is detection of increases in concentration of high boilers in the 6% to 10% range. The catalyst recycle rate is normally adjusted so that the concentration of high boilers in the debutanized liquid oxidate is within the range from about 4% to 6% of such oxidate. That portion of high boilers not recycled can be directed to the TBHP decomposition zone, or if the TBHP decomposition zone is omitted, is the purge stream withdrawn from the process as a by-product stream. The TBHP decomposition zone is maintained at about 340° F. for about 90 minutes. The liquid withdrawn from the TBHP decomposition zone is directed to a distillation zone. A stream comprising TBA is withdrawn overhead from such post decomposition distillation and directed to merge into the liquid fed to the hydrogenation zone. The bottoms from such post-decomposition distillation can be used as a part of the catalyst recycle stream and/or can be disposed of as a fuel for use in burners coping with its soluble catalyst content.

The product obtained from this process of oxidizing mixed butane is a technical grade of TBA containing minor amounts of methanol and isopropanol and possibly still smaller amounts of other oxygenated fuel such as ethanol. Such technical grade of TBA is useful for blending into gasoline.

Example II

A large pressurized kettle has a stirrer maintaining a reasonably uniform mixture while reactants are injected into such liquid reaction mixture in laboratory preparation of tertiary butyl alcohol. A liquid stream of the reaction mixture is directed from the oxidation zone of said kettle to a debutanizing zone. An automatic liquid level control maintains the amount of liquid in the autoclave at a predetermined height. The rate of transfer of each of the liquid streams is regulated in response to the combination of factors comprising reaction rate, temperature, pressure, and reactant injection rate. Any oxygen-containing gas is injected into the oxidation zone to oxidize components. Because air is sometimes at least a component of the oxygen-containing gas the effluent gas often contains nitrogen. Appropriate condensers desirably are positioned between the vapor zone of the autoclave and the gas pressure regulator whereby reflux is directed back to the oxidation zone. The gas withdrawn from the regulator consists of fixed gases such as carbon dioxide, carbon monoxide, air, nitrogen, oxygen, etc. Such gaseous effluent from the autoclave can go through a pressure regulator maintaining the autoclave at a predetermined elevated pressure.

A stream of mixed butanes consisting of normal butane and isobutane is injected into a stirred, pressurized kettle at 290° F. and 600 psig of a system featuring a liquid reaction mixture containing TBHP and more TBA then TBHP and more mixed butanes than the combination of TBA and TBHP. The residence time is about 1.5 hours. The reaction mixture contains 30 ppm of nickel formate. The reaction mixture comprises about 25% oxidate and about 75% mixed butanes.

The effluent stream of liquid is transferred from the oxidation zone and directed through three stages of pilot plant debutanization. The separated butanes are distilled to recover a stream of recycle isobutane, which is pumped back to the oxidation zone. The normal butanes are withdrawn from the bottoms of the butane isomer distillation zone. The debutanized effluent is sent to a distillation zone for separation a low boiling stream from a high boiling stream, the cut point being about 194° F. The high boiling stream is directed through a TBHP decomposition zone, and to a distillation zone for the recovery of a TBA stream, leaving a residual liquid. The TBA stream is combined with the low boilers and directed to the hydrogenation zone. The mixture at about 200 psig is directed to the hydrogenation zone. A catalyst consisting of 3% cobalt oxide and 7% molybdic oxide on a sorptive alumina is employed in hydrogenating methyl ethyl ketone to secondary butyl alcohol and acetone to isopropanol at 220° F. at 200 psig at a space rate of 20 weights of light boiling mixture per weight of catalyst per hour. The effluent from the hydrogenation zone is used as a technical grade of TBA suitable for blending into gasoline.

Example III

An oxidation reaction zone is maintained at about 290° F. at a pressure of about 550 psig. The liquid reaction mixture consists of about 56% mixed butanes and 44% oxidate. The acetone concentration is 3.3%. The concentration of TBA is about 25%. The concentration of water, methanol, and other by-products amounts to about 3.5%. The liquid contains 15 ppm of an equal molar mixture of molybdenum formate and cobalt formate catalyst. Based upon the amount of liquid in the reaction zone, controls establish the operability of the process with a catalyst consisting of finely divided (thus distributable) particles using either cobalt or molybdenum. The TBHP concentration is variable, but the TBA/TBHP unit weight ratio is consistently greater than 2. The residence time is about 5 hours.

The effluent stream withdrawn from the oxidation zone is monitored both as to composition and as to flow rate, aiming to maintain a conversion of isobutane which is about 15% to about 45% of the rate of isobutane feed. The flow rate of such liquid effluent from the oxidation zone is regulated to maintain a concentration of high boiling by-products which is within a range from about 1% to about 10% preferably 2 to 6% of the oxidate. Such liquid effluent from the oxidation zone is directed through a debutanizer to a distillation zone from which a TBA stream is distilled. The residue from such distillation is directed to a TBHP decomposition zone in which the TBHP is decomposed during a period of about 3 hours by heating at 280° F. at about 100 psig. A stream of TBA is distilled from the liquid effluent from the TBHP decomposition zone, leaving as a residue a stream of high boilers. The TBA stream derived from such TBHP decomposition is merged with the principal stream of TBA and directed to a hydrogenation zone. The stream of high boilers is divided so that a portion is directed as a catalyst recycle stream and the balance is withdrawn as a purge stream. The catalyst recycle stream is modulated to maintain 1 to 10% preferably 4 to 6% high boilers. From the product withdrawal zone, there is withdrawn a stream having TBA as the principal component and containing measurable amounts of isopropanol and methanol.

Example IV

The oxidation reaction zone is maintained at about 276° F. at about 600 psig. The liquid reaction mixture contains 25 ppm of solubilized manganese formate catalyst. The liquid contains about 4% TBHP.

The composition of the liquid in the reaction zone is about:

| Mixed butanes | | 60 |
|---|---|---|
| Normal butane | 20 | |
| Isobutane | 40 | |
| Acetone | | 2 |
| TBA | | 32 |
| TBHP | | 4 |
| Others | | 2 |

An effluent stream of the reaction mixture is sent through a debutanizer and distillation zone. The bottoms fraction form the distillation zone is directed to a TBHP decomposition zone and then to a distillation zone for the recovery of a supplemental stream of TBA. Both the primary stream of TBA (from the overhead from distillation of the debutanized oxide) and secondary stream of TBA are directed to a hydrogenation zone effective in converting acetone to isopropanol. The residue remaining after recovery of the primary TBA stream is recycled, while the residue from recovery of the secondary stream of TBA is purged from the process, the regulation of the catalyst recycle and purge being adapted to maintain the concentration of high boilers (other than water and TBHP) in the oxidate within the range from 1 to 10% desirably within 4 to 6% of such oxidate.

Example V

Mixed butanes consisting of about 100 parts of normal butane and about 198 parts of isobutane are reacted with 510 parts of air per hour in a pressurized reaction zone maintained at 285° F. and 500 psig using 450 ppm of finely divided metallic molybdenum as catalyst. About 414 parts of fixed gases ($N_2$, $CO_2$, CO, etc.) are withdrawn through the regulator automatically maintaining the system at 500 psig.

A stream of liquid reaction mixture is withdrawn from the oxidation zone. This liquid, comprising TBA, TBHP, acetone, methanol, formic acid, SBA, MEK, acetic acid, ethanol, NBA, water, esters, and others is directed thru a debutanizing zone and thence to a zone for the separation of an overhead primary stream boiling below 194° F. from the bottoms stream directed to the TBHP decomposition zone. The effluent from the TBHP decomposition zone is distilled to provide an overhead secondary stream of TBA and a residual high boiling stream. The composition of the debutanized oxidate is monitored so that the concentration of miscellaneous high boilers (excluding water, TBHP, NBA and SBA) in said debutanized oxidate is maintained within the range from 1 to 10%, desirably 4 to 6% by withdrawing as a purge stream an appropriate portion of what otherwise would be a catalyst recycle stream. The primary and secondary streams of TBA are directed through a hydrogenation zone so that the TBA stream withdrawn as product contains minor amounts of isopropanol and methanol.

Various modifications of the invention are possible without departing from the scope of the claims.

The invention claimed is:

1. A method of preparing tertiary butyl alcohol which includes the steps of:

separating most $C_3$ hydrocarbons and most $C_5$ hydrocarbons from a mixed $C_4$ hydrocarbon stream in a crude butane purification zone to provide a stream of purified mixed $C_4$ hydrocarbons consisting essentially of from about 51 to about 85% isobutane and from about 49 to about 15% normal butane;

mixing said stream of purified mixed $C_4$ hydrocarbons with a stream of recycle $C_4$ hydrocarbons and with a catalyst stream in a feedstream preparation zone to provide a feedstream of mixed $C_4$ hydrocarbons, said catalyst being distributable in said mixed $C_4$ hydrocarbons, and said catalyst comprising a multivalent metal selected from the group consisting of chromium, cobalt, nickel, manganese, molybdenum, and mixtures thereof in a concentration of from about 1 to about 500 parts per million parts of isobutane, said catalyst stream optionally including a recycled stream derived from a high boiling stream;

maintaining in an oxidation zone, a pressurized liquid reaction mixture, said $C_4$ hydrocarbons derived from the feedstream being the most abundant component of said liquid reaction mixture;

directing said feedstream into said oxidation zone at a feedstream rate controlled to maintain said predominance of $C_4$ hydrocarbons in said liquid reaction mixture in said oxidation zone while maintaining an isobutane flow rate corresponding to a preselected residence time for the $C_4$ hydrocarbons;

injecting an oxygen containing gas into said oxidation zone at a normal rate stoichiometrically effective for converting to tertiary butyl alcohol at least one-sixth but less than half of said isobutane flow rate in said feedstream;

withdrawing from said oxidation zone a stream of liquid reaction mixture at a rate stoichiometrically equal, as regards $C_4$ components, to said feedstream rate and controlled to maintain the residence time of $C_4$ hydrocarbons in said oxidation zone at a predetermined residence time within a range from about 1 to about 10 hours;

maintaining the pressure in said oxidation zone at a predetermined pressure within a range from about 200 to about 1000 psig;

directing a portion of the vapors from said oxidation zone into a reflux zone and withdrawing gaseous products from said reflux zone at a rate adapted to maintain said predetermined pressure, said withdrawn gaseous products comprising oxygen and carbon dioxide;

maintaining the temperature in said oxidation zone substantially at a predetermined temperature within the range from 260° to 340° F., the combination of controlled temperature, pressure, catalyst concentration, high boiler concentration, and residence time providing a conversion of isobutane within the range from 15% to 45%;

subjecting the liquid effluent from the oxidation zone to a debutanizing distillation zone and separating and withdrawing overhead from said debutanizing zone an intermediate mixed butanes stream and separating and withdrawing a residual liquid stream of oxygenated organic liquid from said debutanizing zone;

subjecting said intermediate mixed butanes stream to distillation in a butane isomer distillation zone to prepare a residual normal butane stream containing less than 45% isobutane and an overhead isobutane stream which in isobutane and containing less than 45% impurities comprising normal butane and withdrawing from the process said residual normal butane stream, and directing to said feedstream preparation zone said isobutane stream as a stream of recycle isobutane, subjecting said liquid stream of oxygenated organic liquid from the debutanizing zone to a distillation separation zone for the separation of at least one low boiling stream comprising overhead components selected from the group consisting of acetone, methanol, tertiary butyl alcohol, methyl ethyl ketone, methyl formate, ethyl formate, isopropyl formate, methyl acetate, ethyl acetate, and related compounds boiling below about 194° F., and for the separation of a residual high boiling stream comprising components selected from the group consisting of water, formic acid, secondary butyl alcohol, normal butyl alcohol, tertiary butyl hydroperoxide, acetic acid, high boiling esters, and related compounds boiling above about 194° F.;

subjecting a stream comprising said low boiling stream to hydrogenation in a hydrogenation zone at mild conditions favoring minimized hydrogenation of tertiary butyl alcohol to isobutane and significant conversion of methyl ethyl ketone to secondary butyl alcohol, and acetone to isopropanol, the liquid effluent from the hydrogenation zone being directed to a product separation zone;

optionally subjecting at least a portion of said residual high boiling stream to a tertiary butyl hydroperoxide decomposition zone, the effluent from which is distilled in a post-decomposition distillation zone for separating overhead a supplemental tertiary butyl alcohol stream from a residual effluent stream and directing said supplemental tertiary butyl alcohol stream to said hydrogenation zone, said tertiary butyl hydroperoxide decomposition zone being maintained at a temperature within the range from about 200° to about 350° F. for a residence time of about 1 to about 6 hours;

withdrawing from the process at least a portion of streams selected from the group consisting of said high boiling stream from the separation zone, said residual effluent stream from the post-decomposition distillation zone, and mixtures thereof;

optionally recycling to said feedstream preparation zone a portion of streams selected from the group consisting of said high boiling stream from the separation zone, said residual effluent stream from the post-decomposition zone, and mixtures thereof, as a catalyst recycle stream;

and withdrawing in a product separation zone as the most valuable product of the process a liquid product stream containing minor amounts of isopropanol and methanol, said liquid product stream containing tertiary butyl alcohol as the principal component.

* * * * *